May 19, 1959 H. C. SWIM Plant Pat. 1,835
ROSE PLANT
Filed May 21, 1958
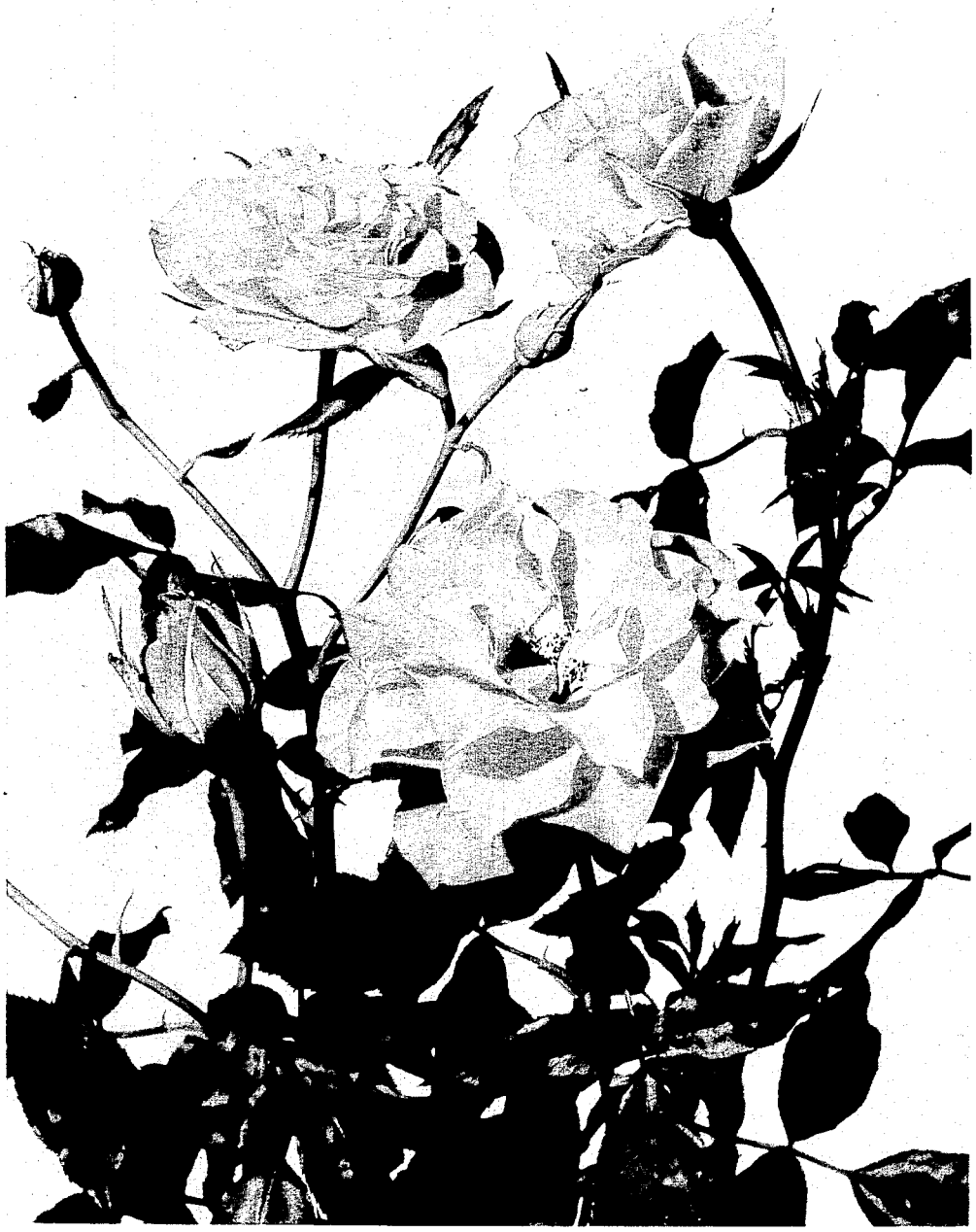
Inventor.
H. C. Swim
By: Robb & Robb
Attorneys.

United States Patent Office

Plant Pat. 1,835

Patented May 19, 1959

1,835

ROSE PLANT

Herbert C. Swim, Ontario, Calif., assignor to Armstrong Nurseries, Inc., Ontario, Calif., a corporation of California Application May 21, 1958, Serial No. 736,941

1 Claim. (Cl. 47—61)

The present invention relates to a new and distinct variety of rose plant of a class between the hybrid tea and floribunda classes, which was originated by me by crossing the variety "First Love" (Plant Patent No. 921) with the variety "Roundelay" (Plant Patent No. 1,280).

The primary objective of this breeding was a part of a broad objective of producing new and improved varieties of a type between the hybrid tea and the floribunda classes, with particular regard to the flower form and flower color in the range of pink and red. Included among the objectives sought were the characteristics of vigorous and floriferous plant habits, with the flowers borne on stems of at least a medium length, either singly or in few flowered clusters. In the present variety, most of the aforementioned objectives have been fully achieved, along with other desirable improvements, as evidenced by the following unique combination of characteristics which are outstanding in the new variety and which distinguish it from its parents, as well as from all other varieties of which I am aware:

(1) Very vigorous and upright-spreading plant habits;

(2) Foliage having better-than-average resistance to mildew;

(3) Leaflets having a shape somewhat more slender than that of the average garden rose variety;

(4) Very floriferous flowering habit, with the flowers borne both singly and sometimes in few flowered clusters, and usually on stems of medium length;

(5) A flower size ranging from medium to large, with moderately double petalage and having an attractive open-flower form particularly notable because of the very pointed petals which often have a tendency to fold longitudinally near the apex; and (6) An outstandingly brilliant general color tonality of the flowers ranging between Cherry and Rose Red.

In comparison with its seed parent, "First Love," the flowers of the new variety are borne more often in few flowered clusters, while those of "First Love" are nearly always borne singly; the new variety is slightly more double in petalage; and the flower color ranges between Cherry and Rose Red, whereas that of this parent is light pink.

As compared with its pollen parent, "Roundelay," the new variety's leaflets are quite slender and more acute in shape at the base than those of this parent; the flowers are less double in petalage; the flower petals are usually quite pointed, instead of quite flat at the apex like those of "Roundelay;" and the flowers are somewhat lighter in color, falling in the range between Cherry and Rose Red, as distinguished from the flower color of this parent, which ranges between Currant Red and Cardinal Red.

Asexual reproduction of the new variety by budding, as performed at Ontario, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Midway between hybrid tea and hybrid polyantha.

Breeding: Seedling.

*Seed parent.*—"First Love."

*Pollen parent.*—"Roundelay."

Propagation: Holds its distinguishing characteristics through succeeding propagations by budding.

*Flower*

Locality where grown and observed: Ontario, California.

Flowers borne: Sometimes singly, but usually from 3 to 5 per stem; in irregular clusters; on stems of from short to medium length and of from normal strength to strong.

Quantity of bloom: Abundant, outdoors.

Continuity: Nearly continuous during growing season.

Fragrance: From slight to moderate.

Bud:

*Peduncle.*—From average length to long; average caliper; from bending to erect; usually smooth; from few to numerous stipitate glands. Color—near Yellowish Oil Green, Plate V (Ridgway), overlaid with near Brick Red, Plate XIII (Ridgway) on the side exposed to the sun.

*Before calyx breaks.*—Size—medium. Form—medium length; pointed; ovoid.

*As calyx breaks.*—Color—near Cardinal Red, Plate 822/2, page 168 (Wilson).

*Sepals.*—Inner surface lined with fine, woolly tomentum; outer surface usually smooth; alternate margins lined with fine, woolly tomentum; other margins lined with a few stipitate glands and slender foliaceous appendages; usually sepals have foliaceous parts extending beyond the tip of the bud equal to ⅔ or more of its length.

*As first petal opens.*—Size—average. Form—medium length; from ovoid to urn-shaped. Color: outside—near Cherry, Plate 722/3, page 157 (Wilson); inside—between Rose Red, Plate 724, page 158 (Wilson) and Rose Red, Plate 724/1, page 158 (Wilson).

*Opening.*—Opens up well; is not prevented from opening by cold, hot, wet or dry weather.

Bloom:

*Size (when fully open).*—From average to large; from 3½ inches to 4 inches.

*Petalage.*—Double; from 26 to 30 petals, plus from 0 to 4 petaloids; arranged regularly.

*Form.*—High-centered at first, but becoming from open to cupped; petals at first being somewhat tightly cupped with tips reflexed slightly outward, but later becoming more loosely flat-cupped at maturity, with tips reflexed outward and often tending to fold near the apex along a longitudinal line terminating at the apex.

Petals:

*Texture.*—Medium thickness; moderately leathery. Inside—slightly velvety. Outside—satiny.

*Shape.* — Outside — broadly obovate, with apex pointed. Intermediate — obovate, with apex pointed. Inside—obovate, with apex somewhat pointed.

This description of a newly opened flower was made from a rose grown outdoors in the month of September at Ontario, California:

*Color.*—Outer petal: outside surface—near Cherry, Plate 722/3, page 157 (Wilson), with small area at base of petal near attachment near Mimosa Yellow, Plate 602/2, page 143 (Wilson); inside surface—near Rose Red, Plate 724/2, page 158 (Wilson), with small area at base of petal near attachment near Mimosa Yellow, Plate 602/2, page 143 (Wilson). Intermediate petal: outside surface—near Cherry, Plate 722/3, page 157 (Wilson), with small area at base of petal near attachment near Mimosa Yellow, Plate 602/2, page 143 (Wilson); inside surface—near Rose Red, Plate 724/1, page 158 (Wilson), with small area at base of petal near attachment near Mimosa Yellow, Plate 602/2, page 143 (Wilson). Inner petal: outside surface—near Cherry, Plate 722/3, page 157 (Wilson), with small area at base of petal near attachment near Mimosa Yellow, Plate 602/2, page 143 (Wilson); inside surface—near Rose Red, Plate 724/1, page 158 (Wilson), with small area at base of petal near attachment near Mimosa Yellow, Plate 602/2, page 143 (Wilson).

This description was made from a rose that was open for three days outdoors in the month of September, at Ontario, California:

*Color.*—Outer petal: outside surface—near Rose Red, Plate 724/3, page 158 (Wilson), with small area at base of petal near attachment near Mimosa Yellow, Plate 602/3, page 143 (Wilson); inside surface—between Rose Red, Plate 724/1, page 158 (Wilson) and Rose Red, Plate 724/2, page 158 (Wilson), with small area at base of petal near attachment near Mimosa Yellow, Plate 602/3, page 143 (Wilson). Inner petal: outside surface—near Rose Red, Plate 724/3, page 158 (Wilson), with small area at base of petal near attachment near Mimosa Yellow, Plate 602/3, page 143 (Wilson); inside surface—near Rose Red, Plate 724/3, page 158 (Wilson), with small area at base of petal near attachment near Mimosa Yellow, Plate 602/3, page 143 (Wilson).

*General color effect.*—Newly opened flower—between Cherry, Plate 722/1, page 157 (Wilson) and Cherry, Plate 722/3, page 157 (Wilson). 3-days open—between Rose Red, Plate 724/2, page 158 (Wilson) and Rose Red, Plate 724/3, page 158 (Wilson).

*Behavior.*—Drop off cleanly; not particularly affected by cold, hot, wet or dry weather.

*Flower longevity.*—On bush in garden—4 or 5 days in November. Cut roses grown outdoors and kept at living-room temperatures—6 or 7 days in November.

*Reproductive organs*

Stamens: From average number to many; arranged regularly about pistils.

Filaments: Medium length; from 5 to 11 mm. in length; most with anthers. Color—near Canary Yellow, Plate 2/2, page 2 (Wilson).

Anthers: Medium size; all open approximately at once. Color: upper side—margins near Yellow Ochre, Plate 07, page 101 (Wilson), with remainder near Mimosa Yellow, Plate 602/2, page 143 (Wilson); under side—margins near Yellow Ochre, Plate 07, page 101 (Wilson), with remainder near Mimosa Yellow, Plate 602/2, page 143 (Wilson).

Pollen: Moderate. Color—near Indian Yellow, Plate 6/1, page 6 (Wilson).

Pistils: Average number; approximately 65 in number.

Styles: Even; from average length to long; from 10 to 15 mm. in length; average caliper; bunched. Color—upper ⅓ of style near Crimson, Plate 22/2, page 22 (Wilson), with remainder near Canary Yellow, Plate 2/3, page 2 (Wilson).

Stigma: Color—near Lemon Yellow, Plate 4/3, page 4 (Wilson).

Ovaries: Usually all enclosed in calyx.

Hips: Average length; from broadly obovoid to globular; moderately smooth; walls thick and fleshy. Color (mature)—near Apricot Orange, Plate XIV (Ridgway), with markings of near Walnut Brown, Plate XXVIII (Ridgway).

Sepals: Falling soon; long; spear-shaped. Color: inside—near Light Grape Green, Plate XLI (Ridgway); outside—near Biscay Green, Plate XVII (Ridgway).

Seeds: Many; from 15 to 25 in number per open-pollinated hip; medium size.

*Plant*

Foliage:

*Leaves.*—Compound of usually 3 to 7 leaflets; abundant; medium size; leathery; semi-glossy.

*Leaflets.*—Shape—from long-oval to oblong; sometimes lancelolate; with apex acute. Base—from obtuse to acute. Margin—simply serrate.

*Color.*—Mature: upper surface—near Leaf Green, Plate XLI (Ridgway); under surface—between Light Grape Green, Plate XLI (Ridgway) and Mytho Green, Plate XLI (Ridgway). Young: upper surface—near Cameo Brown, Plate XXVIII (Ridgway); under surface—near Deep Corinthian Red, Plate XXVII (Ridgway).

*Rachis (the supporting stem of the compound leaf).*—From light to average size. Upper side—grooved; with few stipitate glands on edges. Under side—smooth; with few stipitate glands and from 2 to 4 small prickles.

*Stipules.*—Medium length; narrow; with short points turning out at an angle of more than 45°.

*Disease resistance.* — Better-than-average resistance to mildew, as compared with other varieties grown under comparable cultural conditions at Ontario, California.

Growth:

*Habit.*—Bushy; upright-spreading.

*Growth.*—Very vigorous.

*Canes.*—Heavy.

*Main stems.*—Color—between Parrot Green, Plate VI (Ridgway) and Grass Green, Plate VI (Ridgway). Large prickles—several; from short to medium length; hooked slightly downward; with short, oval base; color—near Cinnamon, Plate XXIX (Ridgway). Small prickles—few; color—near Cinnamon, Plate XXIX (Ridgway). Hairs—none.

*Branches.*—Color—between Biscay Green, Plate XVII (Ridgway) and Light Elm Green, Plate XVII (Ridgway). Large prickles—several; moderately short; hooked slightly downward; with moderately short, narrow base; color—near Chocolate, Plate XXVIII (Ridgway). Small prickles—few; color—near Chocolate, Plate XXVIII (Ridgway). Hairs—none.

*New shoots.*—Color—near Lettuce Green, Plate V (Ridgway). Large prickles—from few to several; medium length; hooked slightly downward; with narrow base of medium length; color—near Ochre Red, Plate XXVII (Ridgway). Small prickles—few; color—near Ochre Red, Plate XXVII (Ridgway). Hairs—none.

I claim:

A new and distinct variety of rose plant of the class falling midway between the hybrid tea and floribunda classes, substantially as herein shown and described, characterized particularly as to novelty by the unique combination of very vigorous and upright-spreading plant habits, foliage of better-than-average resistance to mildew, leaflets having a shape somewhat more slender that that of the average garden rose variety, a very floriferous flowering habit, with the flowers borne sometimes singly but usually in few flowered clusters and on stems of medium length, flowers of from medium to large size and moderately double petalage, said flowers having an attractive open-flower form notable because of the very pointed petals which often have a tendency to fold longitudinally near the apex, and an outstandingly brilliant general color tonality of the flowers ranging between Cherry and Rose Red.

No references cited.